(12) United States Patent
Harrison, III

(10) Patent No.: US 8,197,252 B1
(45) Date of Patent: Jun. 12, 2012

(54) DENTAL COMPOSITE DELIVERY SYSTEM

(76) Inventor: Louie V. Harrison, III, Winona, MS (US)

( * ) Notice: Subject to any disclaimer, the term of this patent is extended or adjusted under 35 U.S.C. 154(b) by 295 days.

(21) Appl. No.: 12/547,622

(22) Filed: Aug. 26, 2009

Related U.S. Application Data

(63) Continuation of application No. 10/766,632, filed on Jan. 28, 2004, now Pat. No. 7,597,556.

(60) Provisional application No. 60/442,989, filed on Jan. 28, 2003.

(51) Int. Cl.
*A61C 5/04* (2006.01)

(52) U.S. Cl. .......................... 433/89; 433/226

(58) Field of Classification Search ............. 433/39, 433/40, 77, 78, 79, 80, 89, 215, 217.1, 226
See application file for complete search history.

(56) References Cited

U.S. PATENT DOCUMENTS

| | | | |
|---|---|---|---|
| 1,133,379 A | | 3/1915 | Hollingsworth |
| 3,265,202 A | * | 8/1966 | Cornell ........................ 206/63.5 |
| 3,756,386 A | | 9/1973 | Marckardt |
| 4,125,190 A | | 11/1978 | Davie et al. |
| 4,303,389 A | | 12/1981 | Salsarulo |
| 4,776,151 A | | 10/1988 | Roth et al. |
| 4,795,527 A | | 1/1989 | Cohen |
| 4,921,137 A | | 5/1990 | Heijenga |
| 4,978,007 A | | 12/1990 | Jacobs et al. |
| 5,015,180 A | * | 5/1991 | Randklev ........................ 433/9 |
| 5,085,585 A | | 2/1992 | Zimble |
| 5,183,397 A | * | 2/1993 | Weissman .................. 433/215 |
| 5,425,635 A | | 6/1995 | Croll |
| 5,472,991 A | | 12/1995 | Schmitt et al. |
| 5,482,464 A | * | 1/1996 | Shimosawa et al. ....... 433/202.1 |
| 5,636,736 A | | 6/1997 | Jacobs et al. |
| 5,660,273 A | | 8/1997 | Discko |
| 5,749,730 A | | 5/1998 | Johnsen et al. |
| 5,762,192 A | | 6/1998 | Jacobs et al. |
| 5,860,806 A | | 1/1999 | Pranitis et al. |
| 5,947,278 A | | 9/1999 | Sawhney et al. |
| 5,989,569 A | | 11/1999 | Dirksing et al. |
| 6,159,009 A | | 12/2000 | Berk et al. |
| D441,090 S | | 4/2001 | Broyles |
| 6,234,793 B1 | | 5/2001 | Brattesani et al. |
| 6,261,094 B1 | | 7/2001 | Dragan |
| 6,343,932 B1 | | 2/2002 | Wiesel |
| 6,394,803 B1 | | 5/2002 | Salz |

(Continued)

*Primary Examiner* — Ralph Lewis
(74) *Attorney, Agent, or Firm* — Wyatt, Tarrant & Combs, LLP; H. Roy Berkenstock

(57) ABSTRACT

A packaged unit of composite for performing an aesthetic restoration. The unit is mounted on a polymeric film carrier material and is covered and sealed with the same or otherwise suitable covering film. The carrier film may be an elongated strip containing serially placed units of composite, each readily separable from the strip for individual usage. This packaging is in light restrictive outer packaging since the preferred unit of composite is of a light-cured material such as bis-GMA. In preferred packaging, the unit dose is singular and applicable to the tooth surface with the film carrier which is adapted with tabs to facilitate handling and the draping or damming of the subject tooth from adjacent teeth to facilitate application of the composite. The composite is then worked, i.e., formed on the tooth with the film intermediate the composite and the customary forming tools. In preferred embodiments, the single unit packaging of composite is mounted on a clear carrier film which includes embrasure tabs for selective insertion in the embrasure between the teeth, and in a further preferred embodiment, the carrier film includes an incisal tab to cover the incisal edge of the tooth. The clear carrier is contained in further outer packaging which limits actinic radiation from reaching the composite.

4 Claims, 3 Drawing Sheets

U.S. PATENT DOCUMENTS

| | | |
|---|---|---|
| 6,506,053 B2 | 1/2003 | Wiesel |
| 6,509,540 B1 | 1/2003 | Summer et al. |
| 6,696,507 B2 | 2/2004 | Subelka et al. |
| 6,986,924 B2 | 1/2006 | Croll |
| 7,537,450 B2 | 5/2009 | Karazivan |
| 7,597,556 B1 * | 10/2009 | Harrison, III .................. 433/89 |

* cited by examiner

DENTAL COMPOSITE DELIVERY SYSTEM

CROSS REFERENCE TO RELATED APPLICATIONS

This application is a Continuation Application (Division) of U.S. patent application Ser. No. 10/766,632, filed Jan. 28, 2004, which claims priority of Provisional Patent Application No. 60/442,989, filed Jan. 28, 2003, the contents of all of which are fully incorporated by reference.

STATEMENT REGARDING FEDERALLY SPONSORED RESEARCH OR DEVELOPMENT

Not Applicable.

REFERENCE TO A "MICROFICHE APPENDIX"

Not Applicable

BACKGROUND OF THE INVENTION

1. Field of the Invention

This invention relates to a method and system for the placement and installation of a synthetic resin composite as an aesthetic restoration of the surface on a tooth, which is otherwise discolored or disfigured.

2. General Background of the Invention

The placement of composites or plastic surfacing or fillings, are widely used as aesthetic restorations. The restorations mimic the natural tooth color and shape to present a "filling" which replaces or resurfaces the defective area of a tooth and thus creates a more pleasing appearance for the wearer. In the application of aesthetic fillings or restorations, it is usual that as soon as the composite material used placed and shaped, it is cured, or polymerized, customarily by light activation, using a special lamp and light guide to direct the high intensity light to the desired locations on the tooth. In the alternative, the composite may be cured by the inclusion of an added agent to promote polymerization, with the set-up of the material occurring without any additional assist. Those skilled in the art recognize that the application of composite and curing process is one which requires particular skill and technique to produce a composite on the tooth which has the requisite strength for long term use.

Common materials utilized in these composites are an acrylic resin which functions as a matrix for other contained materials. The composite may contain filler particles for strength, and color particles for color matching, or opaquers for concealing tooth discoloration. These filler particles are frequently accompanied by a coupling phase which facilitates the bonding of the various components. The resin most commonly used in aesthetic restorations is a bis-GMA, which is the reaction product of bisphenol A and a glycidal methacrylate. The resin is a dimethacrylate monomer which is induced to polymerize by the presence of free radicals (introduced by chemical reaction or by external energy such as heat or light). The chemically activated resins come usually as a two component system—a first paste containing a benzol peroxide initiator and the second containing a tertiary amine activator Immediately prior to application, the two pastes are mixed, i.e., spatulated by hand with such as a spatula or blended by a mixing syringe, such that the amine reacts with the benzoyl peroxide to from free radicals that initiate the polymerization. This spatulated or blended mixture must be promptly applied to the tooth as the polymerization begins immediately, thereby leaving limited time for the dentist to form the restoration.

The light activated resin comes as a single paste, either in a syringe or a compule. The paste contains the photoinitiator module (usually camphroquinone) and an amine activator. When the resin is exposed to a special light, the photoinitiator becomes excited and reacts with the amine to produce the free radicals, which initiate the polymerization process. It should be appreciated that the composite begins to polymerize upon exposure even to normal room light and that the special light the process is accelerated and carried out to a greater depth in the composite.

Whether the resin is applied to the tooth by spatula, syringe or compule, the placement is critical, as is the application of a properly limited amount, neither too much nor too little, so that the formation of the restoration may be affected quickly. The present invention, as will become evident, greatly facilitates the placement of the proper amount of resin for an effective, expedient restoration.

The present invention is directed to a novel packaging of the compule of restorative resin for the expedient aesthetic restoration. Preferably, the resin is the light activated variety which cures primarily when exposed to a curing light. Use of this particular resin provides a much longer (comparatively) "working" time, in that it sets up principally under the curing light, and when exposed, it does so more rapidly than the chemically activated resins. It must be appreciated however, that the light activated resins only cure to the depth of the light penetration, so deep restorations may require the application of multiple layers of resin.

While the choice and application of the particular resin in the aesthetic restoration is of paramount importance, these factors are only part of those considered in the process. Integral steps of the restoration include the draping or damming of the site of the procedure. It is customary in the preparation of a tooth for an amalgam or aesthetic restoration that the tooth be isolated from those around it throughout the procedure. In the instance of application of an aesthetic restoration, care is taken to ensure that the added resin is precluded from contacting adjacent teeth, and keeping the interstices open between teeth. Accordingly, the present invention provides for the packaging and management of a single dose of light activated resin composite, enabling the convenient and efficacious placement of the resin on the selected tooth for working into an aesthetic restoration.

Patents have issued on different dosage and packaging features, from general purpose to special purpose for dental products. By way of example, a patent to Volker Marckardt (U.S. Pat. No. 3,756,386) discloses a multi-chamber container for separately carrying reacting materials which, when mixed, are ready for use as dental composites.

U.S. Pat. No. 4,921,137 to Heijenga discloses a dispensing container for liquid or paste type materials. U.S. Pat. No. 5,947,278 to Sawhney discloses a single-dose, double cup package for dental materials.

U.S. Pat. No. 4,125,190 to Davie, et al. discloses blister packaging which is child resistant.

A patent to Werner Schmidt, et al (U.S. Pat. No. 5,472,991) is directed to a photopolymerizable dental compound for curing in two curing steps.

U.S. Pat. No. 5,636,736 to Jacobs et al. discloses packaging for curable materials, namely orthodontic brackets which are attached to teeth and subsequently connected to retainers and the like for straightening or repositioning teeth. U.S. Pat. Nos. 4,978,007 to Jacobs et al. and 5,762,192 to Jacobs et al. also disclose additional packaging for curable materials.

U.S. Pat. No. 6,159,009 to Berk et al. is discloses an amalgam carrier or syringe for a packaged composite resin for dental restorations. The carrier and replacement sleeves are specifically for carrying light activated resins.

U.S. Pat. No. 6,261,094 to Dragan discloses a syringe for a unit dose of composite materials to a tooth, specifically overcoming stated prior art problems of spatula, palate or like tool. The patent contains a recitation of several patents to capsule syringe dispensers for placement of composite materials.

SUMMARY OF THE INVENTION

The principal objective of the present invention is to provide a packaged unit of composite for performing an aesthetic restoration and a method of applying a restorative with a pre-packaged composite. In the present invention, the unit is mounted on a film carrier material and is covered and sealed with the same or otherwise suitable covering film. The film may be an elongated strip containing serially placed units of composite, each readily separable from the strip for individual usage. This packaging may be enclosed in light restrictive outer packaging since the preferred unit of composite is of a light-cured material such as bis-GMA.

In preferred packaging, the unit dose is singular and the film carrier is adapted with tabs to facilitate the draping or damming of the subject tooth from adjacent teeth to facilitate application of the composite. In preferred embodiments, the single unit packaging of composite carrier film includes embrasure tabs for selective insertion in the embrasure between the teeth, and in a further preferred embodiment, the carrier film includes an incisal tab to cover the incisal edge of the tooth and may also include a gum tab on the side opposite the incisal tab.

In use, the protective cover film is removed from the unit of composite and the single unit is carefully placed over the region of the tooth to be resurfaced, and then the composite is contoured, preferably while the carrier film is still in place by spatuling over the film rather than directly on the composite. In so doing, the surface of the unit composite being worked is not exposed to the air such that an oxygen inhibited layer builds up on the composite which otherwise interferes with the complete curing of the composite applied. Additionally, as those familiar with the procedure, the composite material readily sticks to anything that touches it, including dentists tools such as the spatula. By the inclusion of the film, spatuling may be smoothly accomplished by working the composite under the film without direct contact of the spatula, allowing a much more expedient application with less accumulation of composite on the spatula.

These and other objects and advantages of the invention will become readily apparent to those skilled in the art from the following description of several preferred embodiments taken in conjunction with the included drawings.

DETAILED DESCRIPTION OF PREFERRED EMBODIMENTS

The present invention relates to the field of cosmetic dentistry wherein the visible teeth, such as the incisors and cuspids, if they become diseased, disfigured or discolored, are treated with an aesthetic restoration to improve, if not duplicate the original appearance. This invention is best understood by comparison with the current methods for applying these aesthetic composite restorations.

As related in the Background of the Invention, currently used composites are either mixed immediately prior to application to the tooth followed by being troweled or spatulated on the tooth, to as closely to the final profile as is possible. In working with the mixed composite, working time is limited since the polymerization of the resin begins with the mixing of the two components of the composite. In the instance of the use of a light cured resin, the composite is usually delivered to a tooth from a syringe, and is then spatulated to the final profile. While the polymerization does not begin until the application of a special light source, however the light curable resin attracts oxygen and the exposed surface of the resin becomes somewhat compromised in that it will not cure to the degree as the unexposed material—meaning that working time with the light cured resin is also limited. In both applications, the tooth is cleaned and prepared for the application of the composite. The tooth is dammed, or draped such that it is isolated from the surrounding teeth. The surface of the tooth is etched and then the bonding adhesive is applied, following which the composite is applied as described above. In both applications, the adhesive nature of the composite causes it to stick to the spatula or other working instrument during forming, rendering the application very technique sensitive.

Following the working of the composite to as final a profile as possible, the composite is then further shaped and polished as necessary with the customary rotary tools, including fine diamonds, stones or burrs. The polishing of the surface of the composite to a high gloss is done with discs or rubber tips. It may be necessary to adjust and polish the interproximal surfaces with fine grit finishing strips.

Figure 1:
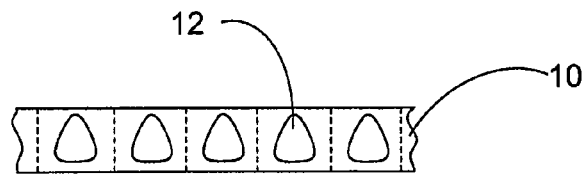
FIG. 1 is a plan view of one embodiment of the invention
Figure 2:
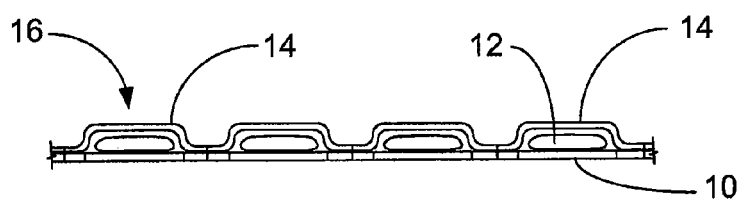
FIG. 2 is a side elevation of the invention shown in FIG. 1.
Figure 7:
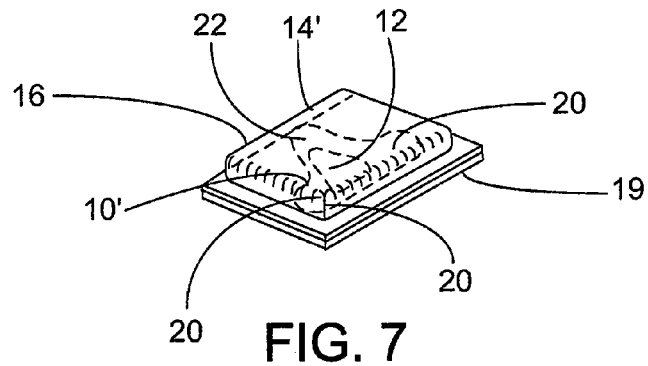
FIG. 7 is a pictorial view of an alternative embodiment of the invention in a singly packaged form.
Figure 5:
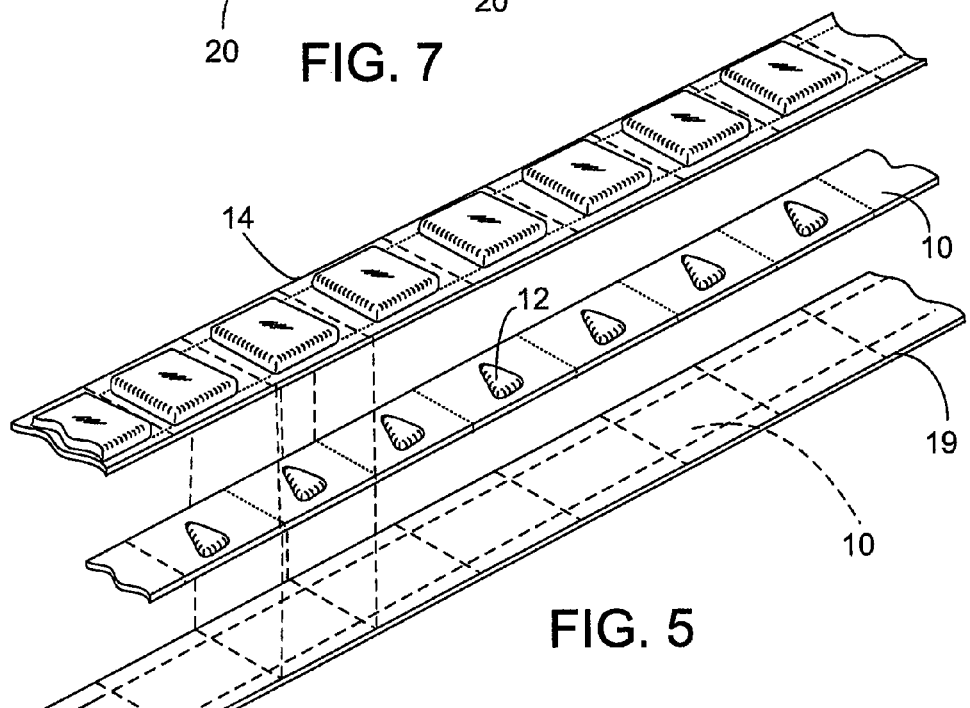
FIG. 5 is an exploded pictorial view of an embodiment in a strip form.
Figure 6:
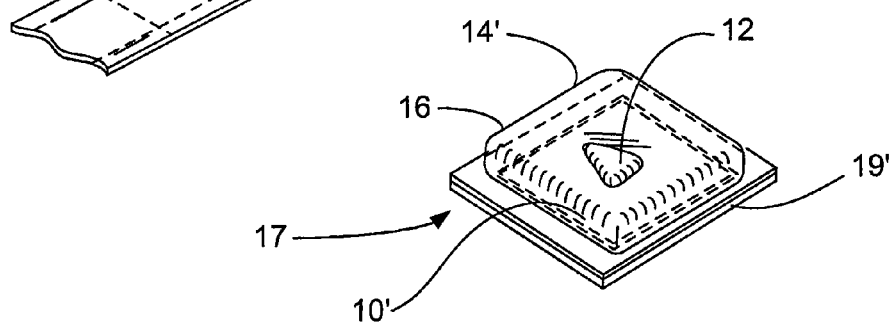
FIG. 6 is a pictorial view of one embodiment of the invention in a singly packaged form.

In order that the present invention might be better appreciated, reference is made to FIGS. 1 and 2 which illustrate one embodiment of the present inventive packaging for a composite to be used in aesthetic restoration. Upon an underlying strip of a carrier 10, a quantity of composite 12, such as a light-activated bis-GMA or other similar material of the type utilized for restorations, is placed. The amount of composite material may vary according to the need anticipated by the dentist. The amount of light-cured composite now available in "single dose" and multiple dose injection ampules varies from about 0.25 to about 0.5 grams in a tip to about 5 to 15 grams per syringe for the syringe applicators. The composite 12 is then covered by a protective layer as cover 14 which is sealed against the carrier around the periphery of the composite 12. The cover 14 may be formed of a variety of materials such as including one of the non-adhesive materials such as silicone, polyethylene or fluoropolymer such as Teflon from E. I. du Pont de Nemours or Silicone Premium from General Electric Company if the cover contacts composite 12. In the alternative, if the cover does not contact the composite, as being a dome-like shape as illustrated in FIGS. 5, 6 and 7, it may be of a formed polystyrene or equivalent material which will withstand deformation in normal handling. The carrier 10 and protective layer 14 may, in turn, also be contained in additional packaging (FIGS. 5, 6 and 7) which restrict light from the composite as well as providing a sterile environment for the packaged composite 12. Preferably, the composite 12 is in a preform (resembling a droplet), somewhat approximating the shape of the tooth upon which to be placed, thereby minimizing the amount of reworking, as by spatula, required by the dentist to get the composite to a final acceptable form on a tooth. In the instances of aesthetic restorations, the applied layer of light-cured composite may be up to about 2 mm in thickness, that thickness approaching the practical limit of curing by light. The composite may include opaquers or colorants to cover stains or cause the color of the restoration to match the adjacent teeth. In the preferred embodiments, the individually packaged composite 12 will be also available in a variety of colors (as now available in the tip or syringe delivery form) in order that the adjacent tooth color may be matched. The subject tooth is prepared in the usual way by cleaning the surface of the tooth and followed by the application of an adhesive to cause the composite to securely adhere to the underlying tooth.

In the illustrated and described embodiments, the underlying carrier 10 is formed of a strong, pliable clear film such as one of the polyester films such as those sold under the trademark MYLAR and by E. I. du Pont de Nemours. "Clear" in this context means translucent to the actinic radiation applied to the composite to cure it. The film carrier 10 should be of a thickness to withstand the spatuling required of the dentist to shape the composite 12 to its final form such that the carrier 10 preferably not be removed until the composite has been worked to substantially its final form on the tooth and cured in place, for reasons later explained. In the preferred embodiments illustrated, the thickness of the carrier 10 is from about 0.025 mm to about 0.25 mm, depending upon the particular film material selected, as in order to provide a sufficient tensile strength and resilience to enable the efficient working of the composite under the film. By not removing the carrier 10 until after curing, the composite is not exposed to the air during spatuling such that any oxygen contamination of the surface of the composite 12 is minimized thereby enabling the curing of the entire exposed surface of the formed composite.

As related above in the Background of the Invention, one of the drawbacks of the light-cured composite material is that on exposure to oxygen, the exposed layer absorbs oxygen from the air, which oxygenated surface resists curing by the light activator through the polymerization of the composite material. Also, by spatuling over the carrier 10, the spatula does not directly contact the composite 12 and accordingly, forming and smoothing the composite to the final shape is facilitated since the composite is not dragged or rolled because of its tendency to stick to the spatula if directly contacted.

As illustrated in FIGS. 1, 2 and 5, the composite 12 may be disposed in sequence on the carrier 10, forming a row of formed ampule-like containers 16 of composite 12 (hereinafter called "compules"). In the illustration, carrier 10 (and the rest of the packaging) is perforated, scored or otherwise weakened at regular intervals intermediate the compules 16. In use of the packaging illustrated in FIGS. 1, 2 and 5, the dentist will break or otherwise tear off a single compule 16 from the carrier 10/strip 19, and once the tooth is prepared to receive the composite, the dentist will remove the cover 14, lift the quantity of composite 12 by removing the carrier from the strip 19 and apply the exposed surface of the composite 12 to the prepared surface of the subject tooth using the carrier 10 to avoid contact between the dentist or adjacent teeth and the composite 12. The dentist will then work or shape the composite with the carrier 10 still in place over the composite, working the composite through the carrier as though it was not there. Once the preferred shape and configuration of composite 12 is achieved, the dentist focuses a curing light, such as an XL 3000 curing light available from 3M of St. Paul, Minn. on the composite 12 through the film. Following the required curing, the dentist then removes the film of carrier 10 and further smoothes and/or polishes the installed composite as needed, by powered polishing wheels or abraders, or by hand tools as is known in the art. As seen in FIGS. 6 and 7, the carrier may be mounted in single packaging strip 19 to which cover 14 is sealed, having therebetween the composite 12 mounted on a carrier 10. If cover 14 and strip 19 constitute the outer packaging of compule 16, both are colored or otherwise made masked to impede any light getting to the composite 12. As previously mentioned, since the composite is oxygen sensitive, it is preferable the compule 16 be sealed against moisture and air, and may be filled with an inert gas to exclude any oxygen absorption. Though not illustrated, compules 16 may be packaged in parallel rows on a strip 19, if preferable.

Figure 3:
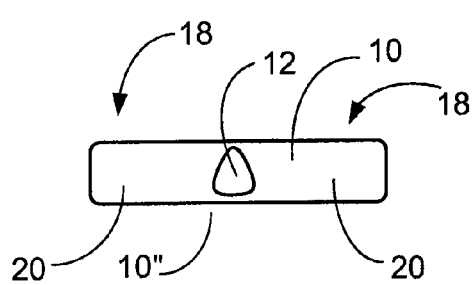
FIG. 3 is a plan view of an alternative embodiment of the invention.
Figure 4:
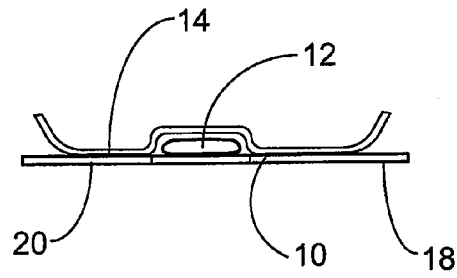
FIG. 4 is a side elevation of the invention shown in FIG. 3.

Referring now to FIGS. 3 and 4, alternative styles of individually packaged compules 16 are illustrated. Figures In FIGS. 3 and 4, compules 16 are individually mounted on a single strip of film carrier 10. The film is of a similar material as in the multiple compule strip illustrated in FIGS. 1 and 2, namely about 0.025 mm in thickness to about 0.25 mm in thickness, and about 1 cm to about 3 cm long and about 0.5 cm to about 1 cm wide. In the single strip embodiment of FIGS. 3 and 4, after the cover 14 has been removed and the composite 12 is to be applied, the tails 18 of the strip may be used for handling the composite to position it on the tooth and as an embrasure tab 20, being placed in the space between the teeth adjacent the subject tooth upon which the restoration is being done. Tabs 20 thus function as handles and also to isolate the composite material 12 from the adjacent teeth during the application of the composite and avoid the necessity to otherwise dam or drape the adjacent teeth with traditional equipment. With this embodiment of the present invention, once the tabs 20 are inserted in the embrasures, the dentist may grasp them with a forceps on the posterior side of the tooth and pull them taught, prior to or as the surface of the compule 16/composite 12 is being smoothed with the spatula. With this dual approach for finishing the restoration, the amount of later contouring or polishing is minimized, and as in the previous embodiment, the composite may be fully cured without concerns over oxygen inhibition.

Figure 8:
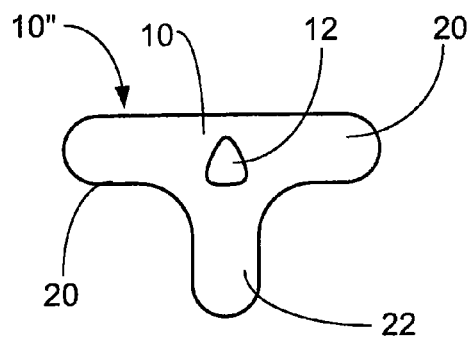
FIG. 8 is a plan view of another alternative embodiment of the present invention.
Figure 9:
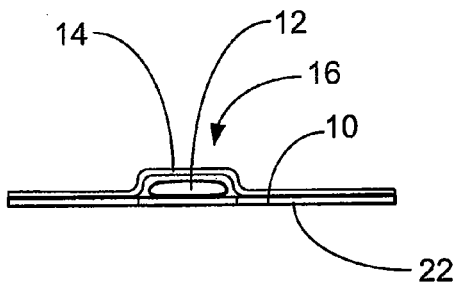
FIG. 9 is a side elevation of the alternative embodiment of FIG. 8.
Figure 10:
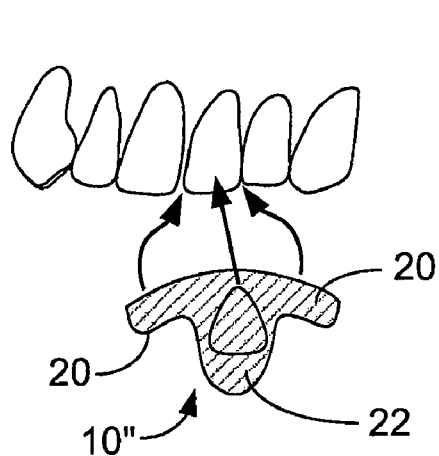
FIG. 10 is a pictorial view of the alternative embodiment of FIGS. 8 and 9 in relation to a tooth.
Figure 11:
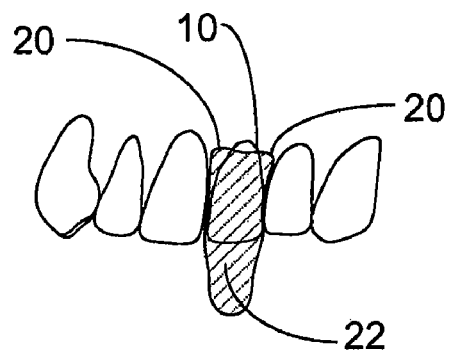
FIG. 11 is a pictorial view of the embodiment of FIG. 10 of the present invention partially mounted on a tooth
Figure 12:
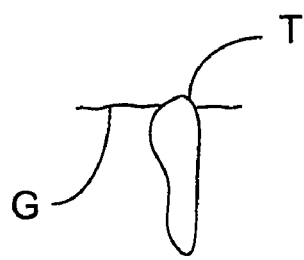
FIG. 12 is side pictorial of a single tooth upon which an alternative embodiment of the present invention shown in FIG. 8, mounted on a tooth.
Figure 13:
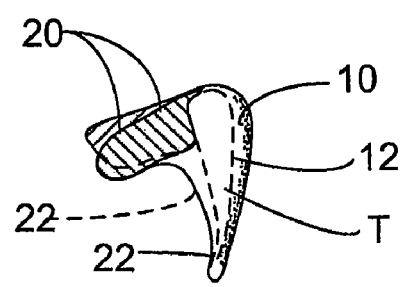
FIG. 13 is a pictorial view of a single tooth and the alternative embodiment of FIG. 11 partially applied thereto.

FIGS. 8 and 9 illustrate a further preferred embodiment for a compule 16, wherein in addition to the embrasure tabs 20, a third tab being an incisal tab 22 is included. FIGS. 10, 11 and 13 illustrate the application of the composite 12 wherein embrasure tabs 20 are interposed between adjacent teeth (FIG. 11) and the incisal tab 22 is folded rearwardly to behind the tooth to position 22' (FIG. 13). After the embrasure tabs 20 are inserted in the embrasure openings, tab 22 is folded tightly over the incisal edge of the tooth, and pulled rearwardly, to further assist in the profiling of the composite 12 to the tooth shape adjacent the incisal edge. The combined pulling of the tabs 20, 22 rearwardly cause composite 12 to be flattened against the tooth, with the edges being flared around the periphery of the tooth T, thereby eliminating much of the forming otherwise required to be done with a spatula. As with the embodiment of FIGS. 3 and 4, any necessary remaining contouring may be done with the spatula, after which the composite is cured with the preferred light source, providing a well cured aesthetic restoration wherein the common problem of an oxygen inhibited composite surface may be minimized, if not totally avoided. Additionally, the features of the tabs for the embrasures and the incisal edges of the teeth facilitate the draping of the tooth as well as the contouring of the composite, thereby reducing the overall time of the procedure as well as greatly facilitating the contouring of the composite which will improve on the aesthetic appearance of the restoration. The embodiments of FIGS. 3 and 4 and 8 and 9 may be packaged individually on an outer strip 19 as illustrated in FIG. 6, however cut to a size commensurate with mounting a single carrier 10 of FIGS. 3, 4 and 7, 9. A single cover 14 may be mounted and sealed over strip 19 thereby creating a single compule 16 incorporating a single carrier 10 and composite 12.

Figure 14:
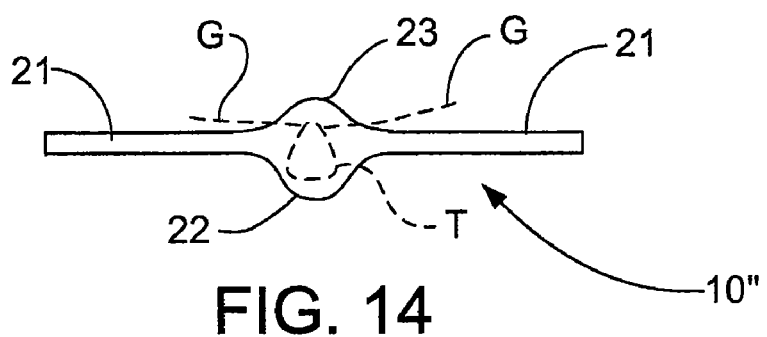
FIG. 14 is a pictorial view of an alternative embodiment of the present invention illustrated in FIG. 10.

FIG. 14 illustrates a further embodiment of the carrier 10, having extended embrasure tabs 21, enabling a further reach behind the tooth for pulling and forming. Likewise, in addition to the incisal tab 22, a gum tab 23 is provided to facilitate working of the composite under the carrier 10 in the region of the gum G. Those skilled in the art that a variety of special forms of tabbed carriers may be provided, each adapted for particular types of restoration.

In the embodiment illustrated in FIG. 5, it is preferred that the strip of compules 16 have an outer package 17, comprised of a sequence of covers 14 which may be similar to the cover illustrated in the embodiments of FIGS. 1 and 2 or supplemental thereto and a continuous strip 19 which may be a film or other moisture and air tight material, such as polyester or ptfe, or another similar material. The outer covers 14 and strip 19 preferably are colored or shaded so as to not be transparent or translucent, at least to the wavelengths of light which are capable of curing composite 12. Additionally, by using such an outer package 17, it is also feasible to provide a plurality of packaged compules 16 wherein the carrier includes tabs such as the embrasure tabs 20 and the incisal tab 22 (as illustrated in FIG. 10) to better enable the handling of the composite 12 and isolation of the adjacent teeth. As illustrated in the individually packaged embodiment illustrated in FIGS. 6 and 7, individual outer packaging of the composite 12 may include a single cover 14' disposed over the composite 12 and singular mounting carrier 10', which are mounted on singular strip 19', wherein differing shapes, colors and dosages of composite 12 may be packaged. By including the outer package 17, whether the compules 16 are in singular or strip form, they may be freely handled in the dentist's office and not be compromised by being exposed to light. It is envisioned that the compules 16, whether in single or strip form will be additionally packaged for transit, as for being placed in inventory and shipped to customers.

The packaging and application of an aesthetic restoration according to the present invention provides significant advantage over those in the present art. Though the use of light curable composites avoid the difficulties of mixing the polymers, there is also significant improvement over current application techniques of light curable polymers. Since the composite is initially laid on the affected tooth, and is manipulated or formed through the carrier film, the spatula or trowel never come directly into contact with the composite.

The composite is characteristically very sticky, and even with experienced use of the trowel or spatula, the material sticks to the instrument during forming of the composite which invariably induces bubbles and voids into the composite which must be worked out, if at all possible. By working the composite through the film, the working time is shortened, is much less sensitive as to technique and provides a more durable and better cure (by the avoidance of bubbles, voids and oxygen absorption and the unhindered smoothing of the composite). The problem of the composite sticking to any of the normally utilized tools is eliminated since it is smoothed to shape under the carrier 10, and cured while still under the carrier, such that when the carrier is finally removed, the composite is cured and there is no longer sticky on its surface. The ability to now package single dose compules enables the providing of a wider variety of colors of composite, and sized dosages to better match the amount required for a single restoration, or multiple restorations, if necessary. Since the aesthetic restoration is commonly done on the central incisor, the lateral incisor or cuspid and the size of these teeth vary from one another, as well as from human to human, the dentist may be assured of a pre-sized, premixed compule which will better match both dosage and color requirement.

With the convenience provided by the inventive packaging and application, the prepackaged/light-cured composite becomes a superior alternative to other mechanisms for the aesthetic restoration. As detailed above, the prepackaged/light-cured composite is clearly easier to use and provides a much more consistently cured end result that either of the mixed polymers for polymerization in place, or the injector applied light-cured composite. The other alternative to these materials is the use of a porcelain veneer, which requires the removal of tooth structure first, to provide a proper base upon which the veneer is fixed with an adhesive, and then shaped, as necessary. The application of a porcelain veneer is quite technique sensitive and not all dentists attempt the technique, which may make it somewhat difficult to find one when the procedure is needed. Secondly, the material and procedure are very expensive, when contrasted to the polymerized composite, whether mixed or light-cured.

PARTS LIST

The following is a list of parts and materials described and illustrated for use in the present invention:

| | |
|---|---|
| 10 | carrier |
| 10' | single carrier |
| 12 | composite |
| 14 | cover |
| 14' | single cover |
| 16 | compule |
| 17 | outer packaging |
| 17' | single outer package |
| 18 | carrier tabs |
| 19 | packaging strip |
| 19' | single package strip |
| 20 | embrasure tab |
| 21 | extended embrasure tab |
| 22 | incisal tab |
| 23 | gum tab |
| G | gum |
| T | tooth |

As will be apparent to persons skilled in the art, various additional modifications, adaptations and variations of the foregoing specifically disclosed embodiments and methods of coating removal may be made without departing form the objectives and scope of the present invention. Various modifications and changes may be made to the embodiments disclosed herein by those skilled in the art and such are contemplated by the present invention and are to be understood as included within the spirit and scope of the appended claims.

What is claimed is:

1. The method of applying an aesthetic dental restoration from a unit package to a tooth, which unit package includes a restoration composite centrally mounted on a carrier film having lateral tabs attached thereto comprising:
    a. placing the composite while on the carrier film adjacent the tooth upon which the restoration is to be applied;
    b. contacting the tooth directly with the composite with the carrier film still mounted thereon by moving said tabs forward toward the adjacent teeth;
    c. contacting the carrier film opposite the composite with a dental composite forming tool and forming the composite to the desired form by working the composite with the film intermediate the composite and the tool;
    d. curing the light-cured composite with the carrier film in place;
    e. removing the carrier film after the composite is cured; and
    f. polishing the composite to its final restorative form.

2. The method according to claim 1 wherein after the tooth is contacted by the composite, the additional steps of placing the tabs into the embrasures between the tooth to which the composite has been applied and the immediately adjacent teeth and tensioning the tabs rearwardly of the tooth thereby spreading the composite over the surface to which applied.

3. The method according to claim 2 wherein the carrier film includes an additional tab positioned centrally of the tabs and extending perpendicularly of the line between the tabs a distance sufficient to be grasped when the composite is placed on the tooth, including the steps of pulling the third tab over the incisal edge of the tooth and rearwardly of the tooth thereby spreading the composite further over the tooth to which applied.

4. The method according to claim 3 including the step of forming the composite to the desired form by working the composite through the film after the composite has been spread by pulling the tabs.

* * * * *